United States Patent
Aho et al.

(12)

(10) Patent No.: US 9,216,230 B2
(45) Date of Patent: Dec. 22, 2015

(54) TREATMENT OF ORGANIC WASTE

(75) Inventors: Seppo Aho, Rovaniemi (FI); Jorma Oinas, Tervola (FI)

(73) Assignee: SAVATERRA OY, Rovaniemi (FI)

( * ) Notice: Subject to any disclaimer, the term of this patent is extended or adjusted under 35 U.S.C. 154(b) by 147 days.

(21) Appl. No.: 13/825,834

(22) PCT Filed: Sep. 26, 2011

(86) PCT No.: PCT/FI2011/050829
§ 371 (c)(1),
(2), (4) Date: Mar. 25, 2013

(87) PCT Pub. No.: WO2012/042108
PCT Pub. Date: Apr. 5, 2012

(65) Prior Publication Data
US 2013/0183745 A1 Jul. 18, 2013

(30) Foreign Application Priority Data
Sep. 28, 2010 (FI) .................................. 20105999

(51) Int. Cl.
*A61L 2/04* (2006.01)
*C05F 9/02* (2006.01)
(Continued)

(52) U.S. Cl.
CPC ... *A61L 2/04* (2013.01); *C05F 9/02* (2013.01); *C05F 17/0027* (2013.01); *C05F 17/0072* (2013.01); *C12M 41/12* (2013.01);
(Continued)

(58) Field of Classification Search
CPC ...... C12M 45/00; C12M 45/02; C12M 45/20; C12M 41/12; C05F 17/0072
See application file for complete search history.

(56) References Cited

U.S. PATENT DOCUMENTS

| 4,134,731 A | 1/1979 | Houser |
| 4,135,908 A * | 1/1979 | Widmer .............................. 71/9 |

(Continued)

FOREIGN PATENT DOCUMENTS

| CN | 1478759 A | 3/2004 |
| CN | 1594225 A | 3/2005 |

(Continued)

OTHER PUBLICATIONS

Search Report dated Jun. 23, 2011 for Finnish Application No. 20105999.
(Continued)

*Primary Examiner* — Jonathan Hurst
(74) *Attorney, Agent, or Firm* — Ladas & Parry LLP

(57) ABSTRACT

There is provided an apparatus for assisting hygienization of organic waste. The apparatus comprises at least one reception means for receiving organic solid matter and organic waste, mixing means for mixing the organic waste and the organic solid matter together into an organic mixture, selecting means for selecting whether to expose the organic mixture in the mixing means to either: aeration in order to create a homogenized and internally oxygenous organic mixture, thereby accelerating the hygienization of the organic mixture, or a heat treatment, wherein the heat treatment performs the hygienization of the organic mixture, or to neither the aeration nor the heat treatment. The mixing means may then expose the organic mixture to the aeration, or to the heat treatment, or to neither of the aeration nor the heat treatment on the basis of the selection. The apparatus may further comprise delivery means for passing the organic mixture to either aerobic biodegradation or an end user.

18 Claims, 3 Drawing Sheets

(51) Int. Cl.
*C05F 17/00* (2006.01)
*C12M 1/33* (2006.01)
*C12M 1/00* (2006.01)
*C12M 1/34* (2006.01)

(52) U.S. Cl.
CPC .............. *C12M 45/00* (2013.01); *C12M 45/02* (2013.01); *C12M 45/20* (2013.01); *Y02W 30/43* (2015.05)

(56) References Cited

U.S. PATENT DOCUMENTS

| | | | | |
|---|---|---|---|---|
| 4,436,817 | A | * | 3/1984 | Nemetz ................. 435/290.4 |
| 5,406,747 | A | * | 4/1995 | Kiefl ...................... 47/1.42 |
| 5,660,124 | A | | 8/1997 | Doncer |
| 5,890,664 | A | * | 4/1999 | Conant, III ................. 241/33 |
| 6,337,203 | B1 | * | 1/2002 | Beaulieu ................. 435/262.5 |
| 6,352,855 | B1 | * | 3/2002 | Kerouac ................. 435/290.3 |
| 2003/0180940 | A1 | | 9/2003 | Watson et al. |
| 2008/0098780 | A1 | * | 5/2008 | Shubin ................... 71/9 |
| 2010/0092652 | A1 | | 4/2010 | Ogura |
| 2010/0132421 | A1 | * | 6/2010 | Aho ....................... 71/12 |

FOREIGN PATENT DOCUMENTS

| | | | |
|---|---|---|---|
| CN | 1762863 | A | 4/2006 |
| CN | 101143758 | A | 3/2008 |
| CN | 201258302 | Y | 6/2009 |
| CN | 101549942 | A | 10/2009 |
| CN | 101679136 | A | 3/2010 |
| CN | 101817699 | A | 9/2010 |
| CN | 101830739 | A | 9/2010 |
| EP | 0 305 782 | A2 | 3/1989 |
| JP | 10-337551 | A | 12/1998 |
| WO | 2005/085156 | A2 | 9/2005 |
| WO | 2008/129127 | A1 | 10/2008 |

OTHER PUBLICATIONS

Patent Abstracts of Japan English abstract of JP 10-337551 A.
Office Action dated Dec. 17, 2013 for Application No. CN 201180047043.X with English translation.
Espacenet English abstract of CN 101143758 A.
Espacenet English abstract of CN 101679136 A.
Espacenet English abstract of CN 1478759 A.
Espacenet English abstract of CN 201258302 Y.
Espacenet English abstract of CN 101830739 A.
Espacenet English abstract of CN 1762863 A.
Espacenet English abstract of CN 1594225 A.
Espacenet English abstract of CN 101817699 A.
Espacenet English abstract of CN 101549942 A.
Xiaoli, Chai, et al., "Compost Principles and Techniques of Solid Waste", Sep. 30, 2005,, pp. 60-65.

* cited by examiner

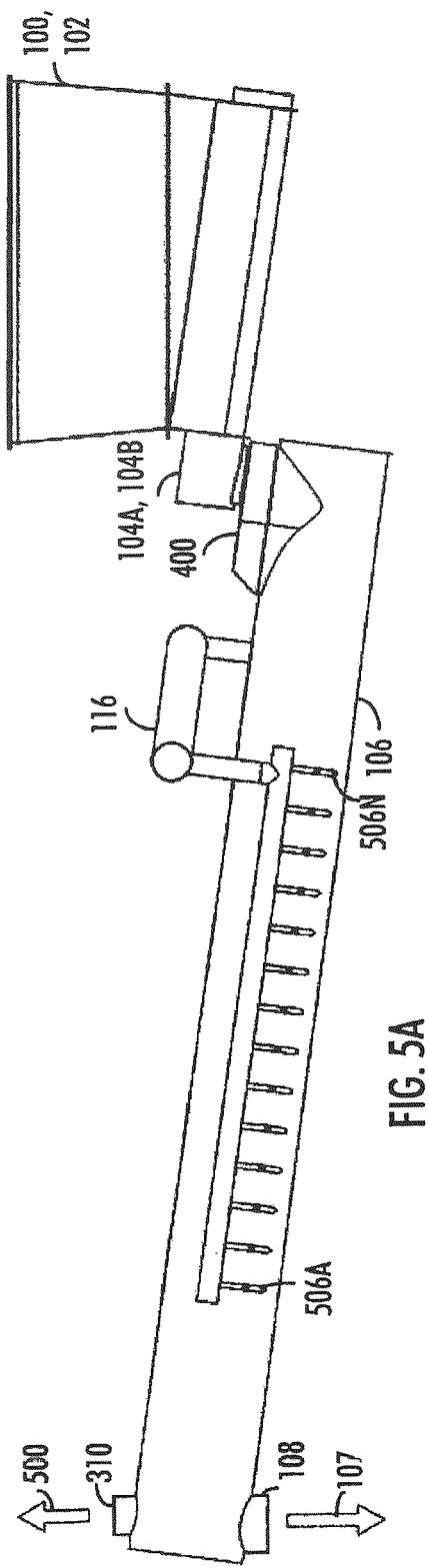
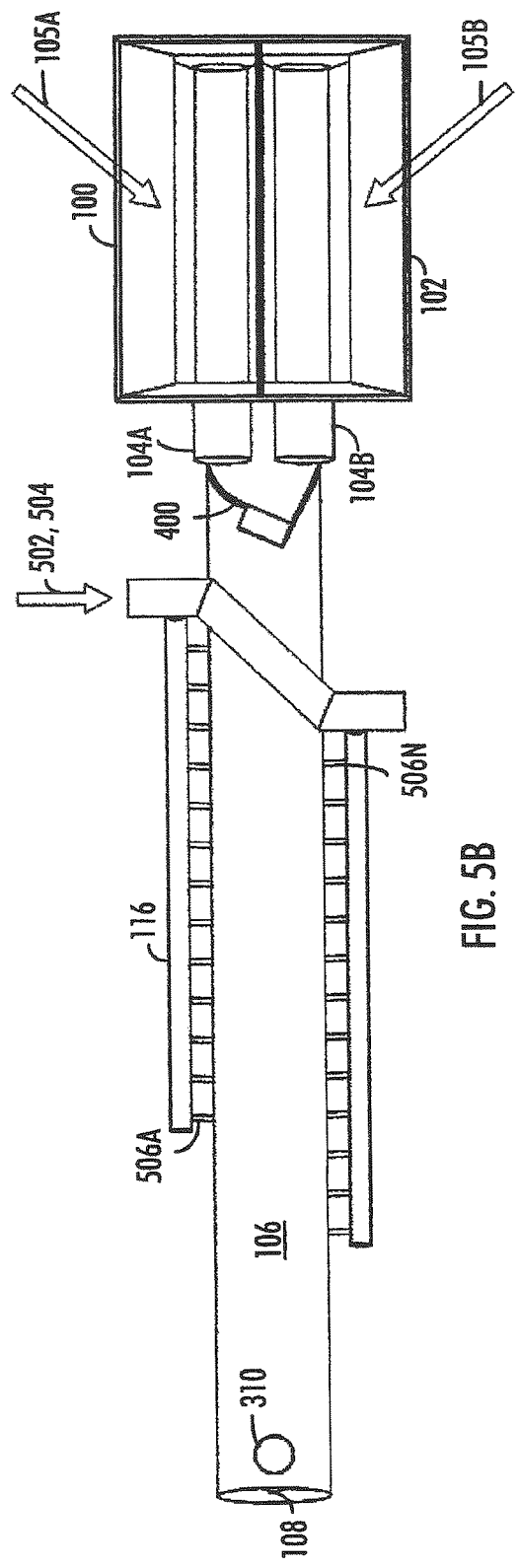
FIG. 5A
FIG. 5B

TREATMENT OF ORGANIC WASTE

FIELD

The invention relates generally to treatment of organic waste, such as sludge. More particularly, the invention relates to an apparatus and a method for treating organic waste.

BACKGROUND

Organic waste, such as sludge, is widely used as a fertilizer. However, the waste is often conditioned to hygienization before it can be used as a fertilizer. The purpose of hygienization is to remove pathogenic microorganisms from biowaste, thus improving the usability of the biowaste as a fertilizer. Common methods for the hygienization include heating of the biowaste or, alternatively, exposing the biowaste to natural hygienization, according to which the biowaste decomposes over time. Both of these types of hygienization solutions are complicated processes and require several separate machines and vehicles which each perform certain steps of the process towards hygienization. This is clearly not an optimal solution for performing the hygienization. Thus, it is important to provide a solution for performing the hygienization in a more optimal manner.

BRIEF DESCRIPTION OF THE INVENTION

Embodiments of the invention seek to improve hygienization of organic waste.

According to an aspect of the invention, there are provided apparatuses as specified in claims 1 and 9.

According to an aspect of the invention, there is provided a method as specified in claim 10. Embodiments of the invention are defined in the dependent claims.

LIST OF DRAWINGS

In the following, the invention will be described in greater detail with reference to the embodiments and the accompanying drawings, in which FIG. 1 presents an apparatus for assisting hygienization of organic waste according to an embodiment;

FIGS. 5A and 5B illustrate an apparatus for assisting hygienization of organic waste according to an embodiment.

DESCRIPTION OF EMBODIMENTS

The following embodiments are exemplary. Although the specification may refer to "an", "one", or "some" embodiment(s) in several locations of the text, this does not necessarily mean that each reference is made to the same embodiment(s), or that a particular feature only applies to a single embodiment. Single features of different embodiments may also be combined to provide other embodiments.

The organic waste may be, for example, sludge. The sludge may be one or more of the following: municipal sludge, agricultural sludge, sewage sludge, i.e. purification plant sludge. The sludge, for instance sludge received from a municipal or another regional waste-water purification plant, may already be biodegraded, i.e. it has been composted, once, and may be used as a starting point. Alternatively, non-decomposed organic waste may be used as the starting material.

As said, the organic waste may comprise sludge from water treatment plants. The sludge can be used as a valuable fertilizer for agricultural soil. However, the use of the sludge as a soil fertilizer is, on one hand, limited by current and local legislation related to the composition of the sludge and, on the other hand, by moral obligations not to cause negative environmental effects, such as odors. The legislation may require for example that the removal of pathogenic microorganisms causing various diseases should take place before the sludge can be used as a fertilizer. As mentioned above this type of hygienization is often obtained by heat treatment, which provides desired results relatively quickly, in few hours, for example.

The hygienization may also take place during composting or biodegradation of organic waste. That is, organic material can be degraded aerobically with oxygen, or anaerobically without oxygen. Composting, on the other hand, is a purposeful application of the biodegradation process. Biodegradation is enabled by the presence of micro-organisms in the organic waste, and it may take a long time. Therefore, it is beneficial to generate the best possible circumstances so that the biodegradation of organic waste is accelerated to decompose quickly and efficiently. "Efficient" herein means that the final product used as a fertilizer still comprises useful nutrients but not pathological micro-organisms.

Figure 1:
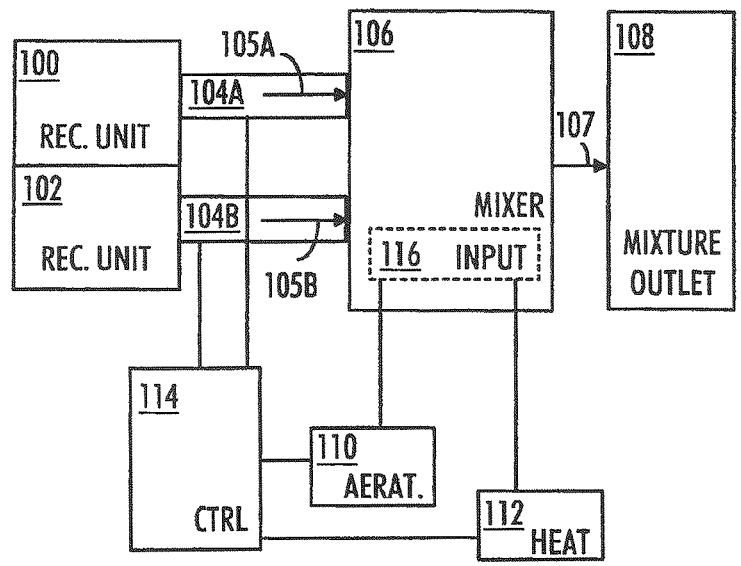

According to an embodiment, there is provided an apparatus for assisting hygienization of organic waste. FIG. 1 shows only elements and functional entities required for understanding the embodiment. Other components have been omitted for reasons of simplicity. The apparatus of FIG. 1 comprises at least one reception unit 100, 102 configured to receive organic waste and solid matter. In an embodiment, there are two reception units 100 and 102, placed next to each other, i.e. side by side. This is advantageous in order for the physical space needed for the reception units 100, 102 to be as small as possible, yet allowing efficient separation of the units 100, 102 and efficient conveyance of materials onwards from the units 100, 102. Basically there may be only one reception unit 100 divided into two separate sub-units, which receive separate materials, such as organic waste and solid material. By situating the reception units side-by-side, wherein a side is denoted as being parallel to the direction of the movement of the material from the units 100, 102 onwards, the space needed is minimized compared to a typical solution where the units 100, 102 are end-to-end, wherein an end is denoted as being perpendicular to the direction of the movement of the material from the units 100, 102 onwards. The receiver unit 100, 102 may be a silo, a tank, or any other unit capable of storing material. It may also be a truck having a trailer or the like.

However, for the sake of simplicity, let us assume that there are two reception units 100 and 102 side by side for receiving the organic waste 105A and the solid matter 105B, respectively. Although the description comprises two reception units 100, 102, there may be more reception units, if necessary. This may be the case when a third material is to be mixed with the solid matter and the organic waste. The waste or the solid matter may be delivered to the receiving unit 100, 102 from anywhere via suitable delivery means. The delivery means may comprise for example tractors, trucks, trailers, etc. Further, the material may be put into the receiver means via a conveyer, such as a screw or a belt conveyer, for example.

According to an embodiment, the solid matter is organic. This means that the solid matter may also be biodegradable matter. Examples of solid matter that may be applied in the process for accelerating biodegradation comprise at least one of the following: peat, pulp, sawdust, green waste, straw, and crushed wood.

The organic waste that is applied in the process may have a dry content of less than 30 per cents. In other words, the organic waste may have a moisture content of 70 per cents or more. According to another embodiment, the organic waste may have a dry content less than 10 per cents. According to an embodiment, the organic waste is sludge, biowaste, or fermentation waste. The sludge may consist of solids separated from wastewater. This type of sludge often contains water between the solid particles, thereby making it difficult to process for biodegradation. For this reason, it is common to mix a certain amount of solid matter with the sludge to make it easier to handle.

The materials from the reception units 100 and 102 may be conveyed onwards via at least one screw conveyer 104A, 104B. That is, each reception unit 100 and 102 may have at least one screw conveyer 104A, 104B for taking the material from the reception units 100, 102 onwards. The use of screw conveyers 104A, 104B is beneficial because a screw conveyer takes only a small space and it is easy to handle. A further advantage of applying a screw conveyer is that it is easy to seal so that the screw conveyers 104A and 104B are closed elements. Moreover, the rotation velocity of each screw conveyer 104A, 104B may be adjusted individually.

Figure 2:
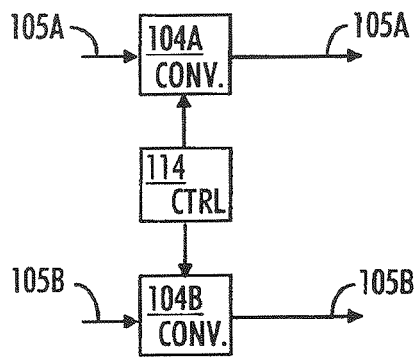
FIG. 2 shows a controller of the apparatus according to an embodiment.

According to an embodiment, as shown in FIGS. 1 and 2, the apparatus may comprise a control unit 114 which may control the rotation velocity of the at least one screw conveyer 104A, 104B so that predetermined relative proportions of the organic waste 105A and the organic solid matter 105B are conveyed onwards. In other words, if the screw conveyer 104A rotates faster than the screw conveyer 104B, the amount of material obtained from the reception unit 100 is larger than the amount of material obtained from the reception unit 102.

In an embodiment, the controller 114 may control the velocities of the screw conveyers 104A, 104B such that the predetermined relative proportions of the organic waste 105A and the organic solid matter 105B to be mixed together are so that the dry content of a resulting organic mixture 107 is between 50 and 60 per cents. Thus, by knowing the initial dry content of the organic waste 105A, the predetermined dry content of the organic mixture 107 may be obtained by appropriately mixing correct proportions of the starting materials. According to an embodiment, the biodegradation process is significantly enhanced when the dry content of the resulting organic mixture is between 50 and 60 per cents. According to another embodiment, the biodegradation period is significantly shortened when the dry content of the organic mixture is between 54 and 56 per cents. Thus, according to an embodiment, the controller 114 may control the velocities of the screw conveyers 104A, 104B such that the predetermined relative proportions of the organic waste 105A and the organic solid matter 105B to be mixed together are such that the dry content of the resulting organic mixture 107 is between 54 and 56 per cents.

Figure 4A:
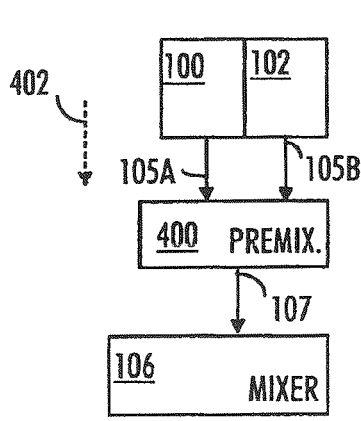
FIGS. 4A and 4B illustrate premixers according to embodiments.

In an embodiment, the mixing of the organic waste 105A and the organic solid matter 105B may be performed, as shown in FIG. 4A, by a premixer 400. The premixer 400 may crush particles in the organic waste 105A and the organic solid matter 105B coming from the reception units 100, 102, respectively, to a predetermined maximum size, thereby accelerating the hygienization. The acceleration results from the fact that the premixer 400 decreases the size of the particles, thereby increasing the surface area of the mixture 107. In addition, the organic mixture 107 becomes lighter in the premixer 400. Lightness of a mixture means that it is internally spacious, i.e. not pressurized or compressed. After the premixer 400, it is also easier for a mixer 106 (to be described later) to work, thus the mixer 106 consumes less power for its functions.

Figure 4B:
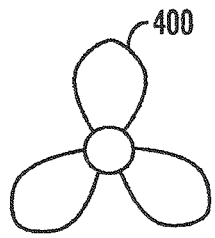

The premixer 400 may be a horizontal-plane premixer 400 when the organic waste 105A and the organic solid matter 105B enter the premixer 400 substantially simultaneously from a substantially vertical direction 402. When looking at the premixer 400 from above (from the direction of the arrow 402), the premixer 400 may look as illustrated in FIG. 4B. The propeller or the paddle type horizontal plane premixer 400 of FIG. 4B may rotate as fast as approximately 600 rounds per minute, although it should be noted that the rotation speed may be controlled by a controller 104 (although not shown in FIGS. 4A/4B).

However, the use of a premixer 400 is not mandatory. As shown in FIG. 1, there is no premixer but only a mixer 106 for mixing the organic waste 105A and the solid matter 105B. The mixer 106 may then mix the organic waste 105A and the organic solid matter 105B together into an organic mixture 107. The mixer 106 may also be called a homogenization chamber for its function to homogenize the material inside the mixer 106. A homogenized structure means that regardless of where a sample of the organic mixture 107 is taken, the sample comprises substantially similar properties.

Figure 3:
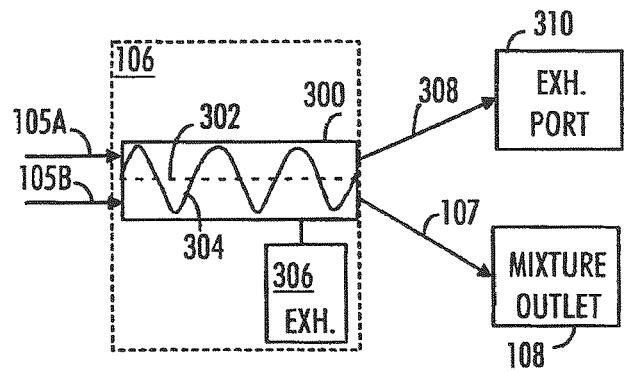
FIG. 3 shows an exhauster according to an embodiment.

The mixer 106 may be a screw conveyer 300 as shown in FIG. 3. The use of the screw conveyer 300 is beneficial owing to its seamless structure, ease of use, and little of space occupied. As stated above, the screw conveyer may be a closed element so that materials or gases within the screw conveyer 300 cannot leak out. The screw conveyer 300 may easily be stopped, either temporarily or permanently, without any leakage of materials or gases from the screw conveyer 300.

The screw conveyer 300 may crush the particles by the motion of the screw. Therefore, by adjusting the velocity at which the screw 304 rotates around the longitudinal axes 302 of the screw conveyer 300, the maximum allowable size of the particles may be determined. Also the form of the screw 304 affects the allowable size of the particles. That is, by applying a screw 304 having a denser screw thread, the maximum allowed particle size may be reduced. Further, according to an embodiment, there may be a net-like wall at an end of the screw conveyer so that the screw conveyer 300 forces the material to pass through the net-like wall. The holes in the net-like wall may be adjusted to obtain the predetermined maximum particle size. The factors affecting the need to adjust the maximum allowable particle size may be at least one of the following: characteristics of the applied organic waste and of the applied solid matter, and characteristics of any further manipulation of the organic mixture. That is, when the solid matter comprises pieces of wood, for example, the size of the wood particles may require reduction before further manipulation of the ingredients.

Let us take another look at FIG. 1, wherein, according to an embodiment, the controller 114 may be responsible for selecting whether to expose the organic mixture 107 in the mixer 106 to aeration in order to create a homogenized and internally oxygenous organic mixture 107, thereby accelerating the hygienization of the organic mixture 107, or to a heat treatment, wherein the heat treatment performs the hygienization of the organic mixture 107, or to neither the aeration nor the heat treatment. The controller 114 may thus be seen as a selection unit for this purpose. The mixer 106 may then expose the organic mixture 107 to either the aeration or the heat treatment on the basis of the selection. That is, the mixer 106 may expose the organic mixture 107 selectively to aeration 110, or to heat treatment 112, or to neither the aeration nor the heat treatment.

For this purpose, according to an embodiment, the mixer 106 may comprise input means 116 for allowing air from an aeration unit 110 or heat from a heat treatment unit 112 to enter the mixer 106. The input means 116 may be a sealable pipe, an opening, or any element capable of transferring the air or the heat from the aeration unit 110 or the heat treatment unit 112, respectively, into the mixer 116. There may be several input means 116 placed along the mixer 106 so that the air or the heat is transferred uniformly into the mixer 106.

In an embodiment, the apparatus comprises an aeration unit 110 and the heat treatment unit 112, so that no input means 116 are necessary. In such a case the aeration unit 110 and the heat treatment unit 112 are directly connected to the mixer 106 to output the air or the heat, respectively, to the mixer 106.

The apparatus may be configured to select which of the two methods to follow because the one and the same apparatus is capable of performing both hygienization procedures. Alternatively, neither of the hygienization methods is to be performed. For this reason, the controller 114 may be connected to the aeration unit 110 and to the heat treatment unit 112 so that the user may control the operations of the two units 110 and 112. The controller 114 may be instructed to perform the aeration process by the aeration unit 110, or to perform the heat treatment by the heat treatment unit 112, for example.

Alternatively, according to an embodiment, the organic mixture 107 in the mixer 106 may be exposed to neither the aeration nor the heat treatment. That is, the controller 114 may select to expose organic mixture 107 to neither the aeration nor the heat treatment. The controller 114 may then instruct the aeration unit 110 and the heat treatment unit not to supply air nor heat to the mixer 106, respectively. This may be advantageous when all that is needed is to mix the materials. In other words, if the organic waste 105A is already hygienized and ready to be used as a fertilizer, but the organic waste 105A needs to be dried by applying the hygienized organic solid matter 105B, then all that is needed is the mixing function of the mixer 106, allowing the use of aeration or heat treatment to be ignored.

The organic mixture 107 to be exposed to either aeration or heat treatment may be fed to the mixer 106, if there is a premixer 400, or the organic mixture 400 may be generated in the mixer 106 when the mixer 106 is the sole element that mixes the organic waste 105A and the organic solid matter 105B together.

The aeration may be performed in order to create a homogenized and internally oxygenous organic mixture 107, thereby accelerating the hygienization of the organic mixture. Thus, the organic mixture 107 is light after being influenced by air in the mixer 106. As the aeration unit 110 introduces, for example, air into the mixer 106, the mixture 107 inside the mixer 106 becomes internally oxygenized by the air entering the spacious organic mixture 107. Thereafter, the organic mixture 107 may comprise a certain volume percentage of oxygen. The spacious, homogenized and internally oxygenous organic mixture 107 is therefore optimally structured for efficient biodegradation and hygienization. The efficiency of the biodegradation may further be increased by controlling the dry matter of the organic mixture 107 to be within the predetermined limits, such as between 50 and 60 per cents. This allows efficient hygienization within two to three months of biodegradation.

The aeration unit may be an air compressor or a similar structure capable of outputting air.

The heat treatment, on the other hand, performs the hygienization of the organic mixture so that no further biodegradation is needed after the mixture 107 exits the apparatus. That is, in terms of hygienization, after the mixer 106 the organic mixture 107 is ready to be used as a fertilizer, for example. In an embodiment, the heat treatment is performed so that the organic mixture 107 is heated with hot air or steam to a temperature of 60 to 100° C., for example.

In an embodiment, the heat treatment is performed so that superheated steam is introduced into the organic mixture 107 in the mixer 106. To generate superheated steam, the heat treatment unit 112 may be a super-heated steam generation unit, which by means of input means 116, such as a pipe, conveys the superheated steam into the mixer 106 and to the organic mixture 107 within the mixer 106. The superheated steam may be a gas mixture generated out of water vapour and combustion gas of a fuel. The fuel which generates the required combustion gas may be light fuel oil, for instance.

The heat treatment may achieve hygienization to destroy pathogenic organisms. The organic mixture 107 may be heated to a temperature of 60 to 100° C. with superheated steam having a temperature of 200 to 600° C. to increase the amount of soluble carbon in the organic mixture 107. As said, the temperature of the superheated steam used in the heating may be between 200 and 600° C. According to the applicant's observations, a temperature range of 300 to 600° C., and particularly 300 to 400° C. is especially suitable in view of the properties of a final product (fertilizer) and thermal economy. The organic mixture 107 may be heat-treated with superheated steam for 20 to 60 minutes. In an embodiment, the heat treatment lasts for 20 to 30 minutes.

An aim of the heat treatment may be to kill pathogenic organisms in the material while intentionally preserving organisms that are advantageous to possible further biodegradation and to the fertilizer. In the hygienization treatment carried out with superheated steam, the material to be purified is heated to a temperature of 60 to 100° C., which is sufficiently high to kill pathogenic organisms but sufficiently low to prevent sterilization of the material to be purified. The heat treatment may additionally aid in destroying seeds of feed. This is especially advantageous when the organic mixture 107 is used as a fertilizer directly after the material exits the apparatus.

The controller 114 may consider each option before determining whether to perform aeration, heat treatment, or neither of them. The selection of which method to perform, or to perform neither of the methods, may be based on the moisture content of the starting materials 105A and 105B, the intended purpose of the resulting organic mixture 107, the required time efficiency of the hygienization process, the space available for the end product, for example. If the starting material is very moist, a need may exist to run the heat treatment in order to dry the resulting organic mixture 107. If the purpose of the organic mixture 107 is to be used as a fertilizer as quickly as possible, the heat treatment may be of use. On the other hand, if time efficiency is of no importance, it may be useful and cost-efficient to perform aeration instead of heat treatment. After the aeration, the organic mixture 107 may need to biodegrade for two to three months, during which time the organic mixture 107 may require storage space. In case of lack of storage space, it may be advantageous to perform the heating process so that the organic mixture 107 may be ready to be used by the end user.

The apparatus may further comprise a delivery outlet 108 for passing the organic mixture 107 to either aerobic biodegradation or an end user. That is, the organic mixture 107 exposed to aeration in the mixer 106 may be conveyed to a suitable biodegradation facility. The time for biodegradation may depend on the moisture content of the organic mixture, for example. In an embodiment, the biodegradation time is two to three months. After the biodegradation, the organic mixture 107 is hygienized and ready to be used as a fertilizer, for example. On the other hand, if the organic mixture 107 is affected by the heat treatment in the mixer 106, the organic mixture is hygienized already in the mixer 106 and the resulting organic mixture 107 may be conveyed to the end user directly to be used as a fertilizer, for example. The delivery outlet 108 may be, for example, a hole at an end of the screw conveyer acting as the mixer 106, or a separate conveyer structure such as a belt conveyer. Thus, the mixture outlet 108 is the only place where the material inside the apparatus exits the apparatus.

The delivery outlet 108 may be part of the mixer 106. That is, the delivery outlet 108 may be implemented at an end of the mixer 106. This is advantageous in order to save physical space.

In an embodiment, the apparatus may further comprise an exhauster 306, as shown in FIG. 3. The exhauster 306 may be for exposing the organic mixture 107 to a suction effect in order to separate undesired gases 308 from the organic mixture 107. That is, especially when heat treatment is performed, the exhauster 306 may be used to remove the undesired gases 308 which result from the heating. An exhaust port 310 may be used to pass the exhausted gases 308 out of the apparatus. The undesired gases to be removed may be odors, for example. The port 310 may be a pipe, a hole, or any transfer means allowing gases to be discharged, for example. The exhauster 306 may be a hoover, or any element capable of generating a low pressure effect to enable a suction effect to occur. The exhaust port 310 may be part of the mixer 106. That is, the exhaust port 310 may be implemented at an end of the mixer 106. This is advantageous in order to save physical space.

The aim of the exhauster 306 is thus to generate a low pressure effect on the organic mixture 107 so that floating gases 308 and/or odors 308 from the organic mixture 107 are removed from the organic mixture 107 before the organic mixture 107 is conveyed to the end user. Similarly, when aeration takes place, the exhauster 306 may be used to remove at least some undesired gases 308 from the organic mixture 107 before the organic mixture 107 is left to biodegrade.

The removed gases 308 may be treated in a separate unit. The separate unit may help in getting rid of the odors in the gases 308 before the gas is allowed to enter the surrounding environment, for example. The separate treatment unit may treat the gases mechanically or chemically, for example. As the mixer 106, being a screw conveyer, may not be completely hollow, the generated low pressure need not be very high in order to perform the suction effect within the mixer 106.

In an embodiment, the exhauster 306 is implemented in connection with the mixer 106 so as to generate a suction effect throughout the mixer 106. This is shown in FIG. 3, where the exhauster 306 generates a low pressure affecting the mixer 106 so as to remove the gases emerging in the mixer 106. This is advantageous to enable the gases to be removed as they emerge due to the heat treatment taking place in the mixer 106, for example.

In an embodiment, the apparatus of FIG. 1 is integrated as one closed structural entity. In other words, the apparatus is one integral, closed structural entity. That is, instead of having separate units, as reception units 100, 102, as the mixer 106, and as the delivery outlet 108, all being connected to each other when used, the units 100, 102, 106 and 108 may be integrated into one closed structural element. The one integral entity may thus be closed such that once the material enters the reception units 100, 102, the material is processed in a closed manner (sealed) within the apparatus until the resulting organic mixture 107 exits the apparatus from the delivery outlet 108. This is advantageous in that gases emerging from the organic mixture 107 within the apparatus may be prevented much more easily than if the units 100, 102, 106, and 108 were separate elements. When the units 100, 102, 106, and 108 are separate elements, junctions between the units 100, 102, 106, and 108 are difficult to make seamless so that no gases can leak from the apparatus.

The compact size of the integral apparatus is possibly due to various features of the apparatus. Firstly, situating the reception units 100, 102 in a side-by-side manner, instead of an end-to-end manner, helps saving space needed for the apparatus, as described earlier.

Secondly, the small space required by the apparatus is enabled by having a screw conveyer as the mixer 106, instead of a drum-like element. The screw conveyer as the mixer 106 may further be capable of performing either aeration or heat treatment. The screw conveyer is also easier to handle and seal than a drum-like mixer. As the screw conveyer is sealed, the screw conveyer may be temporarily stopped without allowing the undesired gases 308, such as odors, to exit (to escape). The gases 308 may exit only through the exhaust port 310 by using the exhauster 306. In a typical drum-like mixer, the gases may relatively easily escape via leakages in the drum. As the drum is significantly more difficult to seal, leakages may easily exist. The stopping of the mixer 106 allows a longer time period for the removal of the gases 308 by the exhauster 306. Without being able to stop the mixer 106, the relatively short physical length of the mixer 106 may result in the undesired gases 308 not being fully removed before the organic mixture exits 107 from the mixture outlet 108.

Thirdly, the small space required by the apparatus is enabled by having the mixture outlet 108 at the end of the mixer 106, preferably as a part of the mixer 106.

In FIG. 5A, the integral apparatus is shown in a side view, whereas FIG. 5B shows the integral apparatus in a top view. The same reference numerals as those used in FIGS. 1 to 4 are applied in FIG. 5 as well. In addition, reference numeral 500 is used to show the gases exiting the apparatus from the exhaust port 310, and reference numerals 502 and 504 are used to show air as used in aeration and heat as used in heat treatment, respectively. As shown in FIG. 5, the one integral structural apparatus may comprise also the premixer 400. The vertically overlapping premixer 400 and screw conveyers 104A and 104B assist in saving the physical space needed for the apparatus. FIG. 5 also shows input means 116 being, according to an embodiment, sealed pipes 506A to 506N along the side of the mixer 106 thus allowing the organic mixture 107 inside the mixer 106 to be uniformly exposed to air or heat. The exhauster applied may be implemented inside the mixer 106.

The physical dimensions of the apparatus may be as follows: length is approximately 20 meters, height is approximately 4.4 meters and width is approximately 3.4 meters. The weight of the apparatus of FIG. 5 may be around 30 tons.

The small and compact size of the apparatus as shown in FIG. 5 is beneficial in that savings in manufacturing and transport costs are significantly decreased. For example, the apparatus may be transported in one semitrailer due to its compact size. Moreover, the maintenance costs will be lower as fewer junctions and elements wear in use and are prone to malfunctions. The maintenance itself will also be easier. As the apparatus is one entity, it is ready to be used at once. Compared to solutions where each unit of an apparatus may be a separate one, the separate units must be connected to each other before usage. The connection of separate entities may result in leakages, and environmentally harmful gases may leak out through those leakages. Thus, the use of one integral structural entity is advantageous.

According to an embodiment, the apparatus of FIG. 5 may comprise at least one reception means for receiving organic solid matter and organic waste, mixing means for mixing the organic waste and the organic solid matter together into an organic mixture, selecting means for selecting whether to expose the organic mixture in the mixing means to either: aeration in order to create a homogenized and internally oxygenous organic mixture, thereby accelerating the hygienization of the organic mixture, or a heat treatment, wherein the heat treatment performs the hygienization of the organic mixture, or to neither the aeration nor the heat treatment. The mixing means may then expose the organic mixture to either the aeration, or the heat treatment, or to neither the aeration nor the heat treatment on the basis of the selection. The apparatus may further comprise delivery means for passing the organic mixture either to aerobic biodegradation or to an end user.

Figure 6:
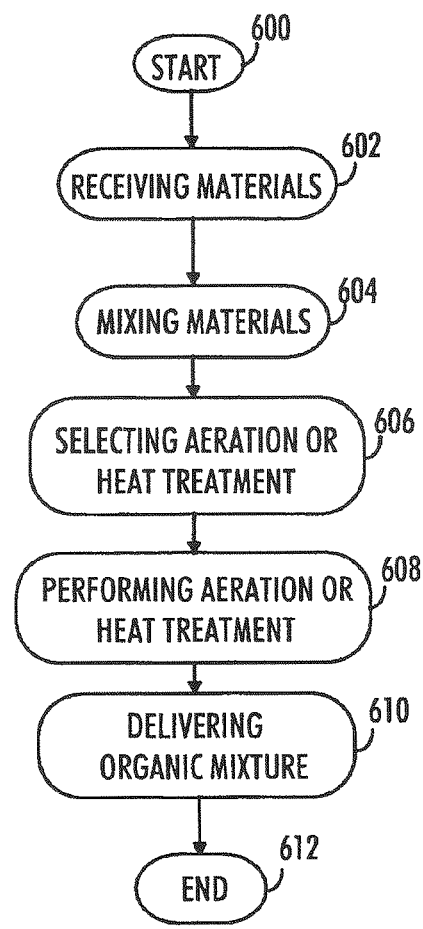
FIG. 6 shows a method of assisting hygienization of organic waste according to an embodiment.

FIG. 6 shows a method for assisting hygienization of organic waste. The method starts in step 600. The method comprises in step 602 receiving organic solid matter and organic waste, in step 604 mixing the organic waste and the organic solid matter together into an organic mixture, in step 606 selecting whether to expose the organic mixture in the mixing means to aeration in order to create a homogenized and internally oxygenous organic mixture, thereby accelerating the hygienization of the organic mixture, or a heat treatment, wherein the heat treatment performs the hygienization of the organic mixture, or to neither the aeration nor the heat treatment. The method may further comprise in step 608 exposing the organic mixture to the aeration, or the heat treatment, or to neither the aeration nor the heat treatment on the basis of the selection, thus performing the aeration or the heat treatment. The method may also comprise in step 610 passing (delivering) the organic mixture to either aerobic biodegradation or an end user. The method ends in step 612.

Even though the invention has been described above with reference to an example according to the accompanying drawings, it is clear that the invention is not restricted thereto but can be modified in several ways within the scope of the appended claims. Further, it is clear to a person skilled in the art that the described embodiments may, but are not required to, be combined with other embodiments in various ways.

The invention claimed is:

1. An apparatus for improving hygienization of organic waste, the apparatus comprising:
   first and second reception units configured to receive organic solid matter and organic waste respectively;
   a first screw conveyer configured to convey the organic solid matter from the first reception unit onwards and a second screw conveyer configured to convey the organic waste from the second reception unit onwards;
   a mixer configured to mix the organic waste and the organic solid matter conveyed from the respective first and second reception units to form an organic mixture;
   first means for aerating the organic mixture in the mixer so as to enable the apparatus to operate in a first mode wherein the organic mixture is hygienized by aeration to create a homogenized and internally oxygenous organic mixture so as to accelerate hygienization of the organic mixture;
   second means for heating the organic mixture in the mixer so as to enable the apparatus to operate in a second mode wherein the organic mixture is heat treated to accelerate hygienization of the organic mixture;
   a controller consisting of a single unit operably connected to the first means for aerating and the second means for heating so that the controller can control operation of both the first means and the second means, the controller being configured (a) to control a rotational velocity of each of the respective first and second screw conveyers based on an initial moisture content of the organic waste and thereby to control a relative proportion of organic waste to organic solid matter conveyed into the mixer to enable attainment of a desired moisture content of the organic mixture in the mixer, and (b) to select whether to expose the organic mixture to aeration from the first means without heat from the second means or to heat treatment from the second means without aeration from the first means so as to control whether the apparatus operates in the first mode or the second mode based on at least one factor selected from the group consisting of a moisture content of material received in the first and second reception units, a desired use of the organic mixture after being hygienized in the mixer, a desired time efficiency of the hygienization and a space available for the organic mixture after being hygienized in the mixer; and
   an outlet configured to allow passage of hygienized organic mixture from the mixer, wherein the mixer defines an enclosed space from which the organic mixture cannot leak out prior to being hygienized and passing through the outlet; wherein the aeration of the organic mixture in the first mode and the heat treatment of the organic mixture in the second mode is performed in the same enclosed space, and wherein the apparatus further comprises a plurality of sealed pipes disposed along the mixer so that air from the aeration or heat from the heat treatment is transferred uniformly into the enclosed space.

2. The apparatus according to claim 1, wherein the mixer comprises input means for allowing entry into the mixer either of air from the first means or heat from the second means.

3. The apparatus according to claim 2, wherein the input means comprises input pipes, and wherein the same input pipes are used for either air from the aeration or heat from the heat treatment to enter the mixer.

4. The apparatus according to claim 1, wherein the controller is configured to control the relative proportion of the organic waste to organic solid matter conveyed to the mixer maintain a dry content of the organic mixture within a preselected range of between 50 and 60 per cent.

5. The apparatus according to claim 1, wherein the mixer is a screw conveyor.

6. The apparatus according to claim 1, wherein the organic solid matter and the organic waste are conveyed to the mixer through a first end of the mixer, and wherein the apparatus comprises means for generating a suction throughout the mixer that exhausts gases from the mixer through an exhaust port at an end of the mixer that is opposite to the first end.

7. The apparatus according to claim 1, wherein the apparatus further comprises a single premixer between the first and second reception units and the mixer, the premixer comprising a propeller configured to crush particles in the organic waste and the organic solid matter to a predetermined maximum size, and wherein the organic waste and the organic solid matter enter the single premixer substantially simultaneously from the first and second reception units.

8. The apparatus according to claim 7, wherein the premixer is a propeller rotating in a horizontal plane.

9. The apparatus according to claim 1, wherein the apparatus is integrated as a single closed structural entity.

10. The apparatus according to claim 1, wherein the second means generates superheated steam having a temperature between 300-400° C.

11. The apparatus according to claim 1, wherein the first and second reception units are disposed side-by-side in the apparatus.

12. The apparatus according to claim 1, wherein the second means for heating applies heat for the heat treatment at a temperature between 300 and 400° C.

13. The apparatus according to claim 1, wherein the controller is configured to control a rotational velocity of each of the respective first and second screw conveyers so that the relative proportions of the organic waste and the organic solid matter are such that a dry content of the organic mixture in the mixer is between 54 and 56 per cent.

14. The apparatus according to claim 1, wherein the controller is configured to select between the first and second mode of operation based on a desired use of the organic waste after hygienization.

15. The apparatus according to claim 1, wherein the controller is configured to select between the first and second mode of operation based on a desired time for hygienization.

16. The apparatus according to claim 1, wherein the controller is configured to select between the first and second mode of operation based an amount of space available for the organic mixture to be passed from the mixer.

17. A method for improving hygienization of organic waste comprising the steps of:
(a) providing the apparatus according to claim 1;
(b) receiving organic solid matter and organic waste in the first and second reception units respectively;
(c) controlling the rotational velocity of the respective screw conveyers so that a predetermined relative proportion of the organic solid matter and organic waste are conveyed onwards from the reception units;
(d) mixing the organic solid matter and the organic waste together in the mixer to form an organic mixture;
(e) causing the controller to select whether the apparatus operates in the first mode by exposing the organic mixture in the mixer to the aeration from the first means without heating from the second means or in the second mode by exposing the organic mixture in the mixer to heat treatment from the second means without aeration from the first means or neither;
(f) exposing the organic mixture to aeration from the first means without heat treatment from the second means or to heat treatment from the second means without aeration from the first means on the basis of the selection in step (e); and
(g) passing the organic mixture either to aerobic biodegradation or to an end user.

18. The method according to claim 17, wherein the controller is caused to make the selection in step (e) based on at least one factor selected from the group consisting of (i) the intended use of the organic mixture; (ii) a required time efficiency of the hygienization; and (iii) an amount of space available.

* * * * *